US006670494B1

(12) United States Patent
Trusovs

(10) Patent No.: US 6,670,494 B1
(45) Date of Patent: Dec. 30, 2003

(54) METHOD FOR PREPARATION OF METAL ORGANIC ACID CHELATES

(75) Inventor: Sergejs Trusovs, Ventura, CA (US)

(73) Assignee: J H Brotech, Inc., Ventura, CA (US)

( * ) Notice: Subject to any disclaimer, the term of this patent is extended or adjusted under 35 U.S.C. 154(b) by 0 days.

(21) Appl. No.: 10/261,610

(22) Filed: Sep. 30, 2002

Related U.S. Application Data

(60) Provisional application No. 60/339,777, filed on Dec. 17, 2001.

(51) Int. Cl.[7] .......................... C07F 13/00; C07F 11/00; C07F 15/00; C25D 1/02
(52) U.S. Cl. ............................... 556/49; 556/1; 556/50; 556/62; 556/63; 556/131; 556/134; 556/147; 556/148; 426/74
(58) Field of Search ............................... 556/1, 49, 50, 556/62, 63, 131, 134, 147, 148; 426/74; 530/400

(56) References Cited

U.S. PATENT DOCUMENTS

| | | | | | |
|---|---|---|---|---|---|
| 4,216,143 | A | * | 8/1980 | Ashmead | 530/400 |
| 4,315,927 | A | | 2/1982 | Evans | 514/188 |
| 4,599,152 | A | | 7/1986 | Ashmead | 205/435 |
| 4,814,177 | A | | 3/1989 | Walsdorf | 424/464 |
| 4,830,716 | A | | 5/1989 | Ashmead | 205/457 |
| 5,504,055 | A | | 4/1996 | Hsu | 504/121 |
| 5,516,925 | A | | 5/1996 | Pedersen et al. | 556/50 |
| 6,166,071 | A | * | 12/2000 | Ashmead et al. | 514/494 |
| 6,294,207 | B1 | * | 9/2001 | Christiansen et al. | 426/74 |
| 6,407,138 | B1 | * | 6/2002 | Ashmead et al. | 514/492 |
| 6,518,240 | B1 | * | 2/2003 | Pedersen et al. | 514/2 |

* cited by examiner

*Primary Examiner*—Porfirio Nazario-Gonzalez
(74) *Attorney, Agent, or Firm*—Ralph D. Chabot

(57) ABSTRACT

A method is disclosed where organic acid chelates can be made by reacting an organic acid ligand with a metal compound in a non aqueous environment. The chelate is thereafter recovered by means of filtration or evaporation.

20 Claims, No Drawings

METHOD FOR PREPARATION OF METAL ORGANIC ACID CHELATES

CLAIM OF PRIORITY

This application claims the priority of US Provisional Application bearing Ser. No. 60/339,777 filed on Dec. 17, 2001.

TECHNICAL FIELD

The invention pertains to the area of chelate preparation in a non-aqueous environment.

BRIEF DESCRIPTION OF THE PRIOR ART

Organic acid chelated transition metals are used as an important trace mineral source for human and animal applications. Certain metal ions are also known to be beneficial in stimulating plant growth and in the production of larger, stronger plants, and for increasing the production of fruits and vegetables. It has become generally accepted that the chelated forms of metals with organic acids are better assimilated by plants, animals, and human beings than are metal salts.

Plant, animal and human tissues show increased metal content when exposed to metal organic acid chelates. Metal organic acid chelates common in the prior art result from reacting a metal ion from a soluble metal salt with an organic acid or its salt; with a mole ratio of one mole of metal to one to three moles (depending on the valency and coordination number of the metal ion) of organic acid to form coordinate covalent bonds.

Organic acid chelates have been generally made in the prior art by reaction using either amino acids, picolinic, nicotinic acids, or hydroxycarboxcylic acids.

Amino and other organic acid chelates are products which result from the reaction of organic acids and a metal ion in the form of either an oxide, hydroxide or salt. In the prior art, for example, amino acid chelates have generally been made by the reaction of one or more amino acids, dipeptides, and polypeptides or protein hydrolisate ligands in an aqueous environment under appropriate conditions which will cause the interaction between the metal and amino acids to form an amino acid chelates.

Metal picolinates are synthesized by the reaction of a metal salt with a picolinic acid salt such as sodium, potassium or ammonium picolinate in a water solution.

Hydroxycarboxcylic acids such as calcium or magnesium citrates are synthesized by the reaction of citric acid with calcium or magnesium oxide, hydroxide or a carbonate water suspension.

Patents indicative of the prior art are U.S. Pat. No. 4,315,927 issued to Evans; U.S. Pat. No. 4,814,177 issued to Walsdorf; U.S. Pat. Nos. 4,830,716 and 4,599,152 issued to Ashmead; U.S. Pat. No. 5,504,055 issued to Hsu; and U.S. Pat. No. 5,516,925 issued to Pedersen. These prior art methods teach the production of metal organic acid chelates produced from either a water solution or paste having a high water content.

Metal organic acid chelates may also be produced in the form of a dry product by some means of drying. As it is well known for those skilled in the art, drying may be accomplished by fluid bed, rotary drum, steam tube, spray, or tray dryer. Drying itself is an energy consuming procedure, technically complicated, and requiring sophisticated equipment. In the case of drum drying, to obtain a final product which is a fine powder, it is also necessary to mill the product exiting the drum.

SUMMARY OF THE INVENTION

Organic acid chelates are made by reacting an organic acid ligand with a metal compound selected from the group consisting of metal oxides, metal hydroxides and metal salts in a non aqueous environment where the quantity of organic acid ligand used corresponds at least to the stoichiometry requirements of the desired metal organic acid chelate to be produced. The chelate is recovered from the suspension by means of filtration or evaporation of the liquid portion of the suspension.

DESCRIPTION OF INVENTION

The present invention eliminates the disadvantages associated with producing organic acid chelates in an initial aqueous environment and describes a method for producing metal organic acid chelates in a substantially non-water media.

The reactants for this process include an organic acid ligand, and a metal compound such as metal oxides, hydroxides, or salts. The organic acid ligand and metal compound are then immersed in a non-aqueous liquid such as, for example, methanol, ethanol, i-propanol, hexane, petroleum ether, etc. and thereafter mixed at room or elevated temperature for a sufficient period of time to allow the reactants to form the desired chelate product.

In some cases, for example, when the non-aqueous liquid used is methanol or other alcohols, the reaction of the organic acid ligand with a metal compound will form a water by-product which will then remain as part of the alcohol solution or solvent.

In other cases, for example, when the non-aqueous liquid used is hexane or petroleum ether, the reaction of the organic acid ligand with a metal compound will also form a water by-product but which may be removed from the reaction media using a Dean Stark water separator or other similar equipment.

The reactants, and their reaction products, i.e. metal organic acid chelates, are highly polar chemical compounds that are insoluble in non-polar organic liquids and form suspensions when added to the non-polar organic liquids. Water is also a reaction product but as described in the preceding paragraphs, can be either removed by water separation equipment or becomes part of the non-aqueous solution; effectively reducing the strength of the alcohol solution to some extent. Therefore, using an organic liquid, rather than water, permits quantitative removal of the metal organic acid chelate produced from the reaction media by simple filtration.

It is well known in the art that organic liquids contain water to some degree and that as used in this specification organic liquids mean substantially water-free liquids and not 100% water free.

Additionally, because both the reactants and products are insoluble in an organic liquid, the liquid may be reused after filtration of the suspension for subsequent metal organic acid chelate synthesis. Furthermore, organic liquid tends to be volatile so the liquid can be removed or separated from the reaction products either by filtration or by drying the chelate either in an open air environment or under vacuum at room temperature.

The metal organic acid chelate product, when allowed to dry, has the physical characteristic of a very fine powder, which does not require subsequent milling.

Metal compounds used in my process can include, but should not be limited to, oxides such as calcium oxide and magnesium oxide; hydroxides such as copper hydroxide, zinc hydroxide, ferrous hydroxide, manganese hydroxide, cobalt hydroxide, and chromium hydroxide; salts such as ferrous sulfate, manganese sulfate, cobalt chloride, and chromium chloride.

Other salts, complexes and chelates of Ca, Mg, Mn, Cu, Zn, Co, Cr, K, Fe and other metals of interest can be mixed with appropriate amounts of citric acid, ascorbic acid, picolinic acid, nicotinic acid, glycine, lysine, glutamic or other organic acids, dipeptides, polypeptides and protein hydrolizates in a non-aqueous liquid such as methanol, i-propanol, hexane, or other non water organic liquid to obtain the desired chelate product which does not require milling subsequent to extraction from the suspension.

The above described method for synthesizing metal organic acid chelates does not require specific sophisticated equipment for drying and milling; therefore, less energy is required for the manufacturing process. The process permits multiple use of the non aqueous liquid, does not produce any waste products, and is environmentally safe.

The following are examples of metal organic acid chelates produced according to my invention. In each example heat is used to boil the suspension. This is done to increase the reaction rate of the process. However, it is not necessary to heat to boiling and furthermore, no heat is necessary for any other reason but to increase the reaction rate.

At the end of each example is a comparison between the theoretical percentage of an element expected to be present and the experimental percentage of the same element obtained from the process. In all examples, the experimental percentage obtained matches closely with the theoretical to establish that the desired chelate was actually produced.

EXAMPLE 1

Calcium Glycinate 5.6 grams (0.1 Mole) of calcium oxide and 15 grams (0.2 Mole) of glycine were placed into a beaker provided with a reflux condenser. 100 ml ethanol was added and the mixture was stirred and boiled at atmospheric pressure for 5 hours. The reaction mixture was then cooled, and thereafter filtered yielding 18.8 grams of calcium glycinate having the physical characteristic of a fine white powder. Approximately 80% of the ethanol solvent was recovered after filtration and may be reused.

Analysis data $Ca_{theoret}$ 21.29%; $Ca_{exp.}$ 20.0%.

EXAMPLE 2

Magnesium Glycinate

The ethanol solvent recovered from Example 1, approximately 80 ml, was distilled to remove any impurities and then combined with fresh ethanol to total 100 ml for this experiment. 4.0 grams (0.1 Mole) of magnesium oxide and 15 grams (0.2 Mole) of glycine were placed into a beaker provided with a reflux condenser. The 100 ml ethanol was added and the mixture was stirred and boiled at atmospheric pressure for 5 hours. The reaction mixture was then cooled, and thereafter filtered yielding 17.2 grams of magnesium glycinate having the physical characteristic of a fine white powder.

Analysis data: $Mg_{theoret}$ 14.09%; $Mg_{exp.}$ 12.8%.

EXAMPLE 3

Copper Glycinate

Copper hydroxide was first formed by dissolving in 100 ml of water 25 grams (0.1 Mole) of copper sulfate pentahydrate and subsequently adding a potassium hydroxide water solution while stirring until the pH of the system stabilized between 10–11. The system reaction mass was thereafter separated using a centrifuge. The separated copper hydroxide precipitate was washed 2 times with ethanol and the recovered copper hydroxide was run through a centrifuge after each ethanol washing.

The copper hydroxide precipitate was then placed into a beaker provided with a reflux condenser and 15 grams (0.2 Mole) of glycine was added. 100 ml of ethanol was thereafter added and the mixture stirred and boiled at atmospheric pressure for 5 hours. The reaction mixture was then cooled and filtered yielding 21.2 grams of copper glycinate in the form of a fine blue powder.

Analysis data: $Cu_{theoret}$ 30.02%; $Cu_{exp.}$ 27.9%

EXAMPLE 4

Zinc Lysinate

Zinc hydroxide was first formed by dissolving in 200 ml of water 13.6 grams (0.1 Mole) of zinc chloride and subsequently adding a potassium hydroxide water solution and stirring until the pH of the system was stabilized between 9–9.5. A centrifuge was used to separate the zinc hydroxide precipitate, and it was washed 2 times with ethanol and the recovered zinc hydroxide was run through a centrifuge after each ethanol washing.

The zinc hydroxide precipitate was then placed into a beaker provided with a reflux condenser and 29.2 grams (0.2 Mole) of lysine was added. 100 ml ethanol was then added to this mixture and stirred and boiled at atmospheric pressure for 3 hours. The reaction mixture was then cooled and filtered yielding 35.5 grams of zinc lysinate in the form of a fine white powder.

Analysis data: $Zn_{theoret}$ 18.38%; $Zn_{exp.}$ 7.1%.

EXAMPLE 5

Ferrous Glutamate

Iron hydroxide in the form of divalent iron was first formed by dissolving in 200 ml of previously boiled water 17 grams (0.1 Mole) of ferrous sulfate monohydrate. The solution was then filtered and a light green liquid filtrate was obtained. Added to this filtrate was a potassium hydroxide water solution and the mixture was continuously stirred until the pH of the solution was stabilized between 9–10. A centrifuge was used to separate the iron hydroxide precipitate, and it was washed 2 times with ethanol and the recovered iron hydroxide was run through a centrifuge after each washing.

The iron hydroxide was then placed into a beaker provided with a reflux condenser and 28 grams (0.1 Mole) of glutamic acid was added. 100 ml ethanol was then added and the mixture was stirred at atmospheric pressure for 5 hours. The reaction mixture was then filtered yielding 30 grams of ferrous glutamate in the form of a fine powder.

Analysis data: $Fe_{theoret}$ 27.65%; $Fe_{exp.}$ 26.8%.

EXAMPLE 6

Ferrous glutamate sulfate 17 grams (0.1 Mole) of ferrous sulfate monohydrate, 28 grams (0.1 Mole) of glutamic acid and 100 ml ethanol were placed into a beaker provided with a reflux condenser. The mixture was stirred and boiled for 5 hours. The mixture was cooled and thereafter filtered yielding 43.2 grams of ferrous glutamate sulfate complex in the form of a fine powder.

Analysis data: $Fe_{theoret}$ 18.74%; $Fe_{exp.}$ 15.3%

EXAMPLE 7

Manganese Glutamate Sulfate 15.1 grams (0.1 Mole) of manganese sulfate, 28 grams (0.1 Mole) of glutamic acid and 100 ml ethanol were placed into a beaker provided with a reflux condenser. The mixture was stirred and boiled for 5 hours. The mixture was then cooled and thereafter filtered yielding 43.1 grams of manganese glutamate sulfate complex in the form of a fine white (slightly pink) powder.

Analysis data: $Mn_{theoret}$ 18.46%; $Mn_{exp.}$ 17.4%.

EXAMPLE 8

Calcium Lysinate 5.6 grams (0.1 Mole) of calcium oxide and 29.2 grams (0.2 Mole) of lysine were placed into a beaker provided with a reflux condenser and a Dean Stark water trap. 100 ml hexane was added and the mixture was stirred and boiled at atmospheric pressure for 5 hours. The reaction mixture was cooled, and was thereafter filtered yielding 32.8 grams of calcium lysinate having the physical characteristic of a fine white powder. In the course of reaction about 3.6–3.8 ml water was removed from the reaction media and acquired in the Dean Stark apparatus.

Analysis data: $Ca_{theoret}$ 12.13%; $Ca_{exp}$ 11.9%.

EXAMPLE 9

Manganese Glutamate

Manganese hydroxide was first formed by dissolving in 200 ml of water 15.1 grams (0.1 Mole) of manganese sulfate and subsequently adding a potassium hydroxide water solution while stirring until the pH of the system stabilized between 11–12. A centrifuge was used to separate the manganese hydroxide precipitate, and it was washed 2 times with ethanol and the recovered manganese hydroxide was run through a centrifuge after each ethanol washing.

The recovered manganese hydroxide was than placed into a beaker provided with a reflux condenser and Dean Stark water trap. 15.5 grams (0.105 Mole) glutamic acid was added. 100 ml hexane was thereafter added and stirred and boiled at atmospheric pressure for 3 hours. During the course of the reaction about 3.6–3.8 ml water was removed from the reaction media and acquired in the Dean Stark apparatus. The reaction mixture was then cooled and filtered yielding 21 grams of manganese glutamate. The product, manganese glutamate, was hygroscopic and requires handling in conditions to avoid absorption of moisture from the air by methods known for those skilled in the art.

Analysis data: $Mn_{theoret}$ 27.32%; $Mn_{exp}$ 25.0%.

EXAMPLE 10

Cobalt Glycinate Chloride 13.0 grams (0.1 Mole) of cobalt chloride, 15.0 grams (0.2 Mole) of glycine and 100 ml ethanol were placed into a beaker provided with a reflux condenser. The mixture was stirred and boiled at atmospheric pressure for 2.5 hours. The mixture was allowed to cool and thereafter filtered yielding 27.8 grams of cobalt glycinate chloride complex in the form of a fine blue powder.

Analysis data: $Co_{theoret}$ 21.20%; $Co_{exp.}$ 20.1%.

EXAMPLE 11

Cobalt Lysinate

Cobalt hydroxide was first formed by dissolving in 200 ml of water 13.0 grams (0.1 Mole) of cobalt chloride and subsequently adding a potassium hydroxide water solution while stirring until the pH of the system was stabilized between 11–12. A centrifuge was used to separate cobalt hydroxide precipitate, and it was washed 2 times with ethanol with the recovered cobalt hydroxide being run through a centrifuge after each ethanol washing.

The recovered cobalt hydroxide was then placed into a beaker provided with a reflux condenser and Dean Stark water trap. 29.2 grams (0.2 Mole) of lysine was added and thereafter 100 ml hexane was subsequently added and stirred and boiled at atmospheric pressure for 3 hours. In the course of reaction about 3.6–3.8 ml of water was removed from the reaction media and acquired in the Dean Stark apparatus. The reaction mixture was then cooled and filtered yielding 35 grams of cobalt lysinate in the form of a fine pink powder.

Analysis data: $Co_{theoret}$ 16.87%; $Co_{exp.}$ 16.1%.

EXAMPLE 12

Chromium Glutamate Chloride 15.85 grams (0.1 Mole) of chromium chloride, 29.4 grams (0.2 Mole) of glutamic acid and 100 ml ethanol were placed into a beaker provided with a reflux condenser. The mixture was stirred and boiled at atmospheric pressure for 3.5 hours. The mixture was cooled and thereafter filtered yielding 43.8 grams of chromium glutamate chloride complex in the form of a fine blue powder.

Analysis data: $Cr_{theoret}$ 11.54%; $Cr_{exp.}$ 10.3%.

EXAMPLE 13

Chromium Lysinate

Chromium hydroxide was first formed by dissolving in 200 ml of water 15.85 grams (0.1 Mole) of chromium chloride and subsequently adding a potassium hydroxide water solution while stirring until the pH of the system stabilized between 11–12. A centrifuge was used to separate the chromium hydroxide precipitate, and it was subsequently washed 2 times with ethanol and the recovered chromium hydroxide was run through a centrifuge after each ethanol washing.

The recovered chromium hydroxide was then placed into a beaker provided with a reflux condenser and Dean Stark water trap. 43.8 grams (0.3 Mole) of lysine was added and thereafter 100 ml hexane was added to this mixture and stirred and boiled at atmospheric pressure for 3 hours. In the course of the reaction about 5.3–5.5 ml of water was removed from the reaction media and acquired in the Dean Stark apparatus. The reaction mixture was then cooled and filtered yielding 48.2 grams of chromium lysinate in the form of a fine blue-gray powder.

Analysis data: $Cr_{theoret}$ 10.66%; $Cr_{exp.}$ 9.5%.

EXAMPLE 14

Calcium Citrate 13.4 grams (0.24 Mole) of calcium oxide and 30 grams (0.16 Mole) of citric acid were placed into a beaker provided with a reflux condenser. 80 ml ethanol was added and the mixture was stirred and boiled at atmospheric pressure for 2 hours. The reaction mixture was cooled and thereafter filtered yielding 39 grams of calcium citrate having the physical characteristic of a fine white powder.

Analysis data: $Ca_{theoret}$ 21.1%; $Ca_{exp.}$ 19.2%

EXAMPLE 15

Magnesium Citrate 9.4 grams (0.24 Mole) of magnesium oxide and 30 grams (0.16 Mole) of citric acid were placed into a beaker provided with a reflux condenser. 80 ml ethanol was added and the mixture was stirred and boiled at atmospheric pressure for 2 hours. The reaction mixture was cooled and thereafter filtered yielding 35 grams of magnesium citrate having the physical characteristic of a fine white powder.

Analysis data: $Mg_{theoret}$ 11.1%; $Mg_{exp.}$ 12.4%.

EXAMPLE 16

Magnesium Nicotinate 8 grams (0.2 Mole) of magnesium oxide, 49.2 grams (0.4 Mole) of nicotinic acid and 150 ml ethanol were placed into a beaker provided with a reflux condenser. The mixture was stirred and boiled at atmospheric pressure for 2 hours. The mixture was cooled and thereafter filtered yielding 53.1 grams of magnesium nicotinate in the form of a fine white powder.

Analysis data: $Mg_{theoret}$ 9.05%, $Mg_{exp.}$ 8.5%.

I claim:

1. A method for preparing a metal organic acid chelate comprising the steps of:
   providing an organic acid ligand;
   providing a metal compound selected from the group consisting of metal oxides, metal hydroxides and metal salts;
   providing a non-aqueous liquid;
   adding to said non-aqueous liquid said organic acid ligand and said metal compound to form a suspension;
   heating said suspension while stirring for a sufficient time to obtain a desired reaction rate which will cause the organic acid ligand and metal compound present to react and form an insoluble metal organic chelate; and,
   filtering said suspension yielding a metal organic acid chelate.

2. The method of claim 1 where said organic acid ligand is selected from the group consisting of citric acid, ascorbic acid, picolinic acid, nicotinic acid, glycine, lysine, glutamic acid, dipeptides, polypeptides and protein hydrolizates.

3. The method of claim 1 where said non-aqueous liquid is selected from the group consisting of methanol, ethanol, i-propanol, hexane, petroleum and ether.

4. The method of claim 1 where said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

5. The method of claim 2 where said non-aqueous liquid is selected from the group consisting of methanol, ethanol, i-propanol, hexane, petroleum and ether.

6. The method of claim 2 where said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

7. The method of claim 3 where said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

8. A method for preparing a metal organic acid chelate comprising the steps of:
   providing an organic acid ligand;
   providing a metal compound selected from the group consisting of metal oxides, metal hydroxides and metal salts;
   providing a non-aqueous liquid;
   adding to said non-aqueous liquid said organic acid ligand and said metal compound to form a suspension,;
   stirring said suspension for a sufficient time to cause the organic acid ligand and metal compound present to react and form an insoluble metal organic chelate; and,
   filtering said suspension yielding a metal organic acid chelate.

9. The method of claim 8 where said organic acid ligand is selected from the group consisting of citric acid, ascorbic acid, picolinic acid, nicotinic acid, glycine, lysine, glutamic acid, dipeptides, polypeptides and protein hydrolizates.

10. The method of claim 8 where said non-aqueous liquid is selected from the group consisting of methanol, ethanol, i-propanol, hexane, petroleum and ether.

11. The method of claim 8 said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

12. The method of claim 9 where said non-aqueous liquid is selected from the group consisting of methanol, ethanol, i-propanol, hexane, petroleum and ether.

13. The method of claim 9 where said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

14. The method of claim 10 where said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

15. A method for preparing a metal organic acid chelate comprising the steps of:
   providing an organic acid ligand;
   providing a metal compound selected from the group consisting of metal oxides, metal hydroxides and metal salts;
   providing a non-aqueous liquid;
   adding to said non-aqueous liquid said organic acid ligand and said metal compound to form a suspension,;

stirring said suspension for a sufficient time to cause the organic acid ligand and metal compound present to react and form an insoluble metal organic chelate; and, evaporating the liquid portion of said suspension to yield a metal organic acid chelate.

16. The method of claim 15 where said organic acid ligand is selected from the group consisting of citric acid, ascorbic acid, picolinic acid, nicotinic acid, glycine, lysine, glutamic acid, dipeptides, polypeptides and protein hydrolizates.

17. The method of claim 15 where said non-aqueous liquid is selected from the group consisting of methanol, ethanol, i-propanol, hexane, petroleum and ether.

18. The method of claim 15 said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

19. The method of claim 16 where said non-aqueous liquid is selected from the group consisting of methanol, ethanol, i-propanol, hexane, petroleum and ether.

20. The method of claim 16 where said metal compound selected from the group consisting of said metal oxides, metal hydroxides and metal salts is either calcium oxide, magnesium oxide, copper hydroxide, zinc hydroxide, ferrous hydroxide, manganese hydroxide, cobalt hydroxide, chromium hydroxide, ferrous sulfate, manganese sulfate, cobalt chloride, or chromium chloride.

* * * * *